US011253209B2

United States Patent
Manzke et al.

(10) Patent No.: US 11,253,209 B2
(45) Date of Patent: Feb. 22, 2022

(54) SPECTRAL IMAGING

(71) Applicant: KONINKLIJKE PHILIPS N.V., Eindhoven (NL)

(72) Inventors: Robert Manzke, Bonebuttel (DE); Roland Proksa, Neu Wulmstorf (DE); Anne Morawski Neubauer, Denver, CO (US); Carsten Oliver Schirra, St. Louis, MO (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 937 days.

(21) Appl. No.: 14/354,191

(22) PCT Filed: Nov. 1, 2012

(86) PCT No.: PCT/IB2012/056091
§ 371 (c)(1),
(2) Date: Apr. 25, 2014

(87) PCT Pub. No.: WO2013/068896
PCT Pub. Date: May 16, 2013

(65) Prior Publication Data
US 2014/0286557 A1  Sep. 25, 2014

Related U.S. Application Data

(60) Provisional application No. 61/558,154, filed on Nov. 10, 2011.

(51) Int. Cl.
*A61B 6/03* (2006.01)
*F24F 3/14* (2006.01)
(Continued)

(52) U.S. Cl.
CPC ............... *A61B 6/032* (2013.01); *A61B 6/12* (2013.01); *A61B 6/4241* (2013.01); *A61B 6/481* (2013.01);
(Continued)

(58) Field of Classification Search
None
See application file for complete search history.

(56) References Cited

U.S. PATENT DOCUMENTS

2005/0283074 A1   12/2005  Jackson et al.
2006/0173362 A1*  8/2006  Toms et al. .................. 600/478
(Continued)

FOREIGN PATENT DOCUMENTS

DE  102008049604 A1   4/2010
GB      2368843 A     5/2002
(Continued)

OTHER PUBLICATIONS

Anke de Vries, Erica Custers, Johan Lub, Sandra van den Bosch, Klaas Nicolay, Holger Grüll, "Block-copolymer-stabilized iodinated emulsions for use as CT contrast agents", Biomaterials, vol. 31, Issue 25, 2010, pp. 6537-6544, ISSN 0142-9612, (Year: 2010).*
(Continued)

*Primary Examiner* — Jiangeng Sun
(74) *Attorney, Agent, or Firm* — Larry Liberchuk

(57) ABSTRACT

An analyzer (124) includes a quantifier (204) configured to quantify an amount of contrast material representing scar tissue created by ablation for tissue of interest in contrast enhanced imaging data and a recommender (210) configured to generate a signal indicative of a recommendation to further ablate the tissue of interest in response to the quantified amount of the contrast material not satisfying a pre-determined threshold. A method includes obtaining contrast enhanced image data indicative of scar tissue created by
(Continued)

Figure 1:
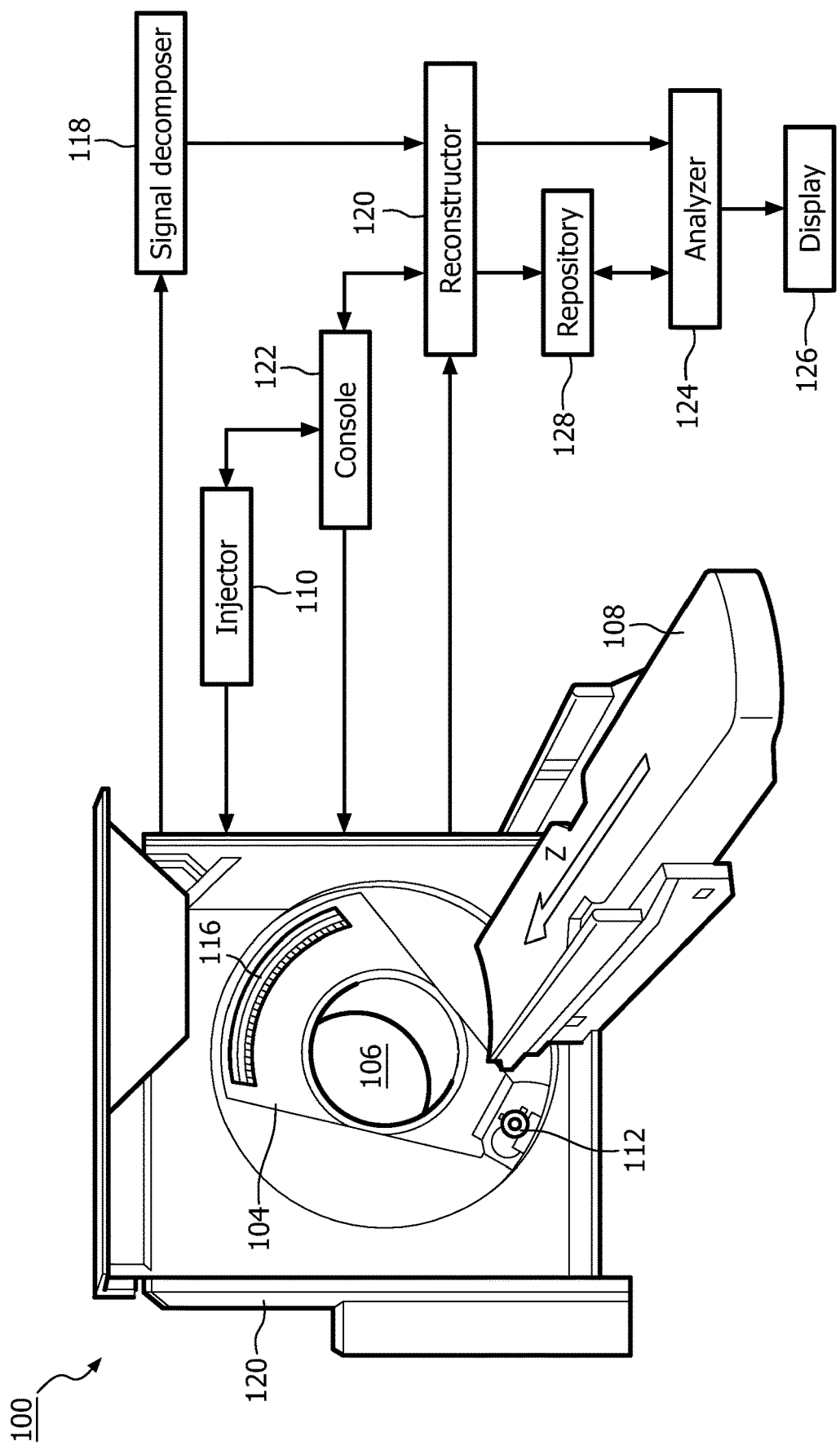

ablation of tissue of interest, quantifying an amount of contrast material for the scar tissue in the tissue of interest, and generating a signal indicative of a recommendation to further ablate the tissue of interest in response to the quantified amount of the contrast material not satisfying a pre-determined threshold.

18 Claims, 3 Drawing Sheets

(51) Int. Cl.
  *F25B 15/14* (2006.01)
  *F25B 1/00* (2006.01)
  *A61B 6/12* (2006.01)
  *A61B 6/00* (2006.01)
  *G06T 7/00* (2017.01)

(52) U.S. Cl.
  CPC .............. *A61B 6/482* (2013.01); *A61B 6/503* (2013.01); *A61B 6/5235* (2013.01); *F24F 3/1417* (2013.01); *F25B 1/00* (2013.01); *F25B 15/14* (2013.01); *G06T 7/0012* (2013.01); *G06T 2207/10081* (2013.01); *G06T 2207/10116* (2013.01); *G06T 2207/20221* (2013.01); *G06T 2207/30048* (2013.01); *G06T 2207/30096* (2013.01); *Y02B 30/62* (2013.01)

(56) References Cited

U.S. PATENT DOCUMENTS

| 2007/0112342 | A1  | 5/2007 | Pearson et al. |
| 2007/0123815 | A1* | 5/2007 | Mark .............................. 604/22 |
| 2008/0147056 | A1  | 6/2008 | Van Der Weide et al. |
| 2009/0054756 | A1* | 2/2009 | Granger ................ G06T 7/0012 600/410 |
| 2009/0086884 | A1  | 4/2009 | Krauss |
| 2010/0008558 | A1  | 1/2010 | Baeumer et al. |
| 2011/0123082 | A1  | 5/2011 | Proksa |

FOREIGN PATENT DOCUMENTS

| RU | 2009102067 A      | 7/2010  |
| WO | WO-2006132651 A2 * | 12/2006 ............. G06T 5/009 |
| WO | 2008078231 A1     | 7/2008  |

OTHER PUBLICATIONS

Kyongtae T. Bae, "Intravenous Contrast Medium Administration and Scan Timing at CT: Considerations and Approaches", radiology.rsna.org, Radiology: vol. 256: No. 1—Jul. 2010, https://doi.org/10.1148/radiol.10090908.*

Carmode et al: "Atherosclerotic Plaque Composition: Analysis With Multicolor CT and Targeted Gold Nanoparticles"; Radiology: vol. 256, No. 3, 2010, pp. 774-782.

Roessl et al: "Preclinical Spectral Computed Tomography of Gold Nano-Particles"; Nuclear Instruments and Methods in Physics Research A, vol. 648 (2011), pp. S259-S264.

* cited by examiner

SPECTRAL IMAGING

CROSS-REFERENCE TO PRIOR APPLICATIONS

This application is the U.S. National Phase application under 35 U.S.C. § 371 of International Application No. PCT/I132012/056091, filed on Nov. 1, 2012, which claims the benefit of U.S. Provisional Patent Application No. 61/558,154, filed on Nov. 10, 2011. These applications are hereby incorporated by reference herein.

The following generally relates to a spectral imaging and is described with particular application to computed tomography (CT); however, the following is also amenable to other imaging modalities such as X-ray and/or other imaging modalities.

Since the absorption of a photon by a material is dependent on the energy of the photon traversing the material, the detected radiation also includes spectral information. A spectral CT scanner additionally captures the spectral information. Generally, a spectral CT scanner includes two or more x-ray tubes configured to emit radiation having different mean spectrums, a single x-ray tube configured to be controllably switched between at least two different emission voltages during scanning, and/or a single broad spectrum x-ray tube and an energy-resolving detector array with energy-resolving detectors (e.g., with photon counting detectors, at least two sets of photodiodes with different spectral sensitivities, etc.) and discrimination electronics. K-edge spectral imaging leverages the phenomena that high-Z elements tend to attenuate photons to a much higher extent above a particular energy (the K-edge energy of the given element) relative to attenuating photons just below the K-edge energy. The discontinuity in the attenuation behavior can be detected using an energy-resolving detector.

Cardiac catheter ablation, generally, is a minimally invasive medical procedure in which a catheter, having a radiofrequency emitter disposed at its tip, is passed within a vessel such as the femoral vein to a particular region of the heart where the emitter is activated to emit an electrical signal to ablate particular tissue such as cardiac cells with abnormal electrical activity, which may lead to arrhythmias. Cardiac catheter ablation has been used to successfully treat supraventricular tachycardia (SVT), atrial flutter, atrial fibrillation (AF) and ventricular tachycardia (VT), and has been performed by human and robot under human control. The success of catheter ablation, for example, of AF, requires continuous lines of scar to encircle the pulmonary veins in the left atrium. Unfortunately, cardiac catheter ablation procedures are often unsuccessful due to the lack of adequate ablation assessment to ensure the suitable ablation of the tissue of interest has been performed.

Aspects described herein addresses the above-referenced problems and others.

In one aspect, an analyzer includes a quantifier configured to quantify an amount of contrast material representing scar tissue created by ablation for tissue of interest in contrast enhanced imaging data and a recommender configured to generate a signal indicative of a recommendation to further ablate the tissue of interest in response to the quantified amount of the contrast material not satisfying a pre-determined threshold.

In another aspect, a method includes obtaining contrast enhanced image data indicative of scar tissue created by ablation of tissue of interest. The method further includes quantifying an amount of contrast material for the scar tissue in the tissue of interest. The method further includes generating a signal indicative of a recommendation to further ablate the tissue of interest in response to the quantified amount of the contrast material not satisfying a pre-determined threshold.

In another aspect, a method includes determining whether ablation of tissue of interest is complete based on contrast enhanced image data indicative of scar tissue created by the ablation for the tissue of interest.

The invention may take form in various components and arrangements of components, and in various steps and arrangements of steps. The drawings are only for purposes of illustrating the preferred embodiments and are not to be construed as limiting the invention.

FIG. 1 schematically illustrates an example imaging system in connection with an analyzer configured to analyze contrast enhanced image data indicative of a contrast material targeted to scar tissue created during and/or after the ablation.

Figure 2:
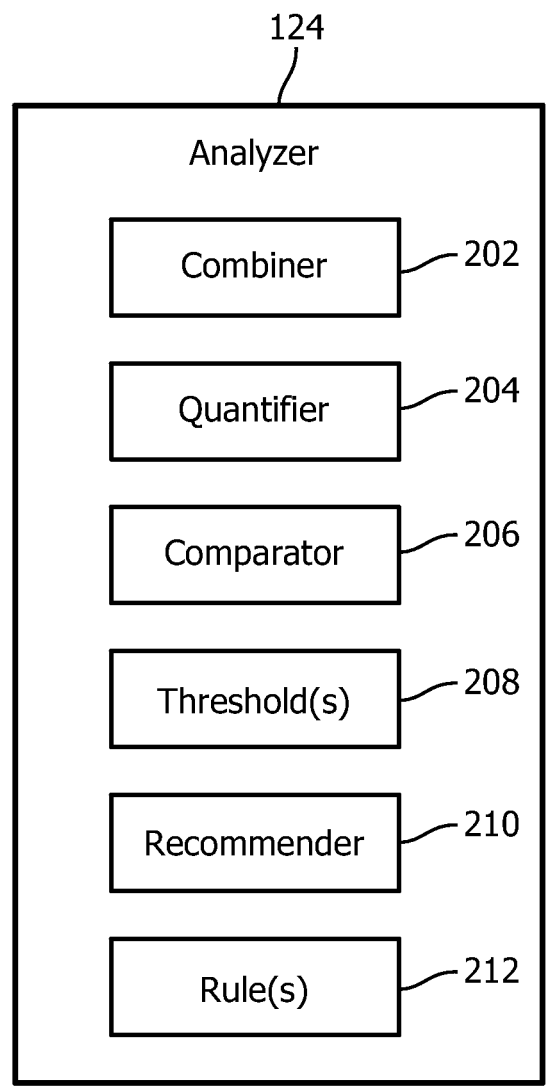

FIG. 2 schematically illustrates an example of the analyzer illustrated in FIG. 1.

Figure 3:
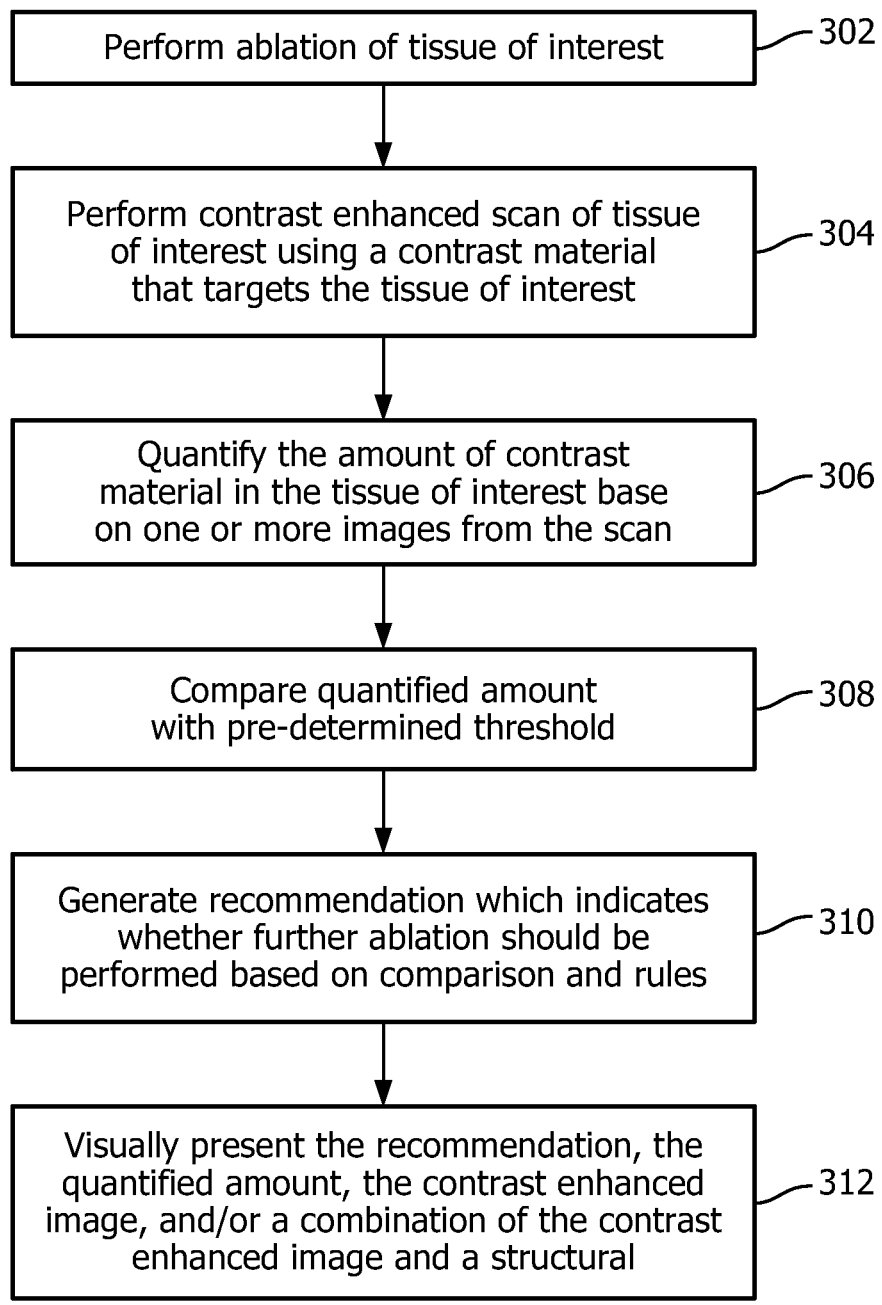

FIG. 3 illustrates an example method for evaluating a result of ablation of tissue of interest.

The following generally relates to utilizing imaging to assess ablation of tissue of interest. As discussed above, cardiac catheter ablation procedures are often unsuccessful due to the lack of adequate ablation assessment to ensure the suitable ablation of the tissue of interest has been performed. As described in greater detail below, the approach herein includes performing a contrast enhanced scan of scar tissue created by ablation using a contrast agent targeted to the scar tissue and analyzing the resulting image(s) to assess the ablation. In one non-limiting instance, the assessment can be utilized to determine whether further ablation should be performed, thereby mitigating unsuccessful ablation due to lack of adequate ablation assessment.

FIG. 1 illustrates an example imaging system 100 such as a computed tomography (CT) system. The imaging system 100 includes a generally stationary gantry 102 and a rotating gantry 104, which is rotatably supported by the stationary gantry 102. The rotating gantry 104 rotates around an examination region 106 about a longitudinal or z-axis. A subject support 108 such as a couch supports a subject such as a human or animal patient or an object in the examination region 106. The subject support 108 is movable in coordination with scanning so as to guide the subject or object with respect to the examination region 106 for scan of the subject or object.

An injector 110 is configured to administer a contrast material(s) to a subject or object, for example, in connection with a contrast enhanced imaging procedure such as a contrast enhanced imaging procedure performed during and/or after cardiac catheter ablation to image contrast material concentrated in scar tissue resulting from the ablation. The illustrated injector 110 is controlled by the system 100, which activates the injector 110 to administer a contrast material in coordination with scanning. The injector 110 may alternatively be activated by a clinician and/or other authorized personnel. Alternatively, the contrast material is manually administered by the clinician and/or authorized personnel.

A suitable contrast material includes a targeted (tissue-specific) contrast agent with nano-particles having a K-edge within the diagnostic x-ray energy band (e.g., 20-140 keV). The specific tissue, in one non-limiting instance, includes scar tissue, macrophages, inflammation, and/or other physiological change created by cardiac catheter ablation at the time of the ablation. In another instance, the specific tissue is a tumor. The nano-particles can include one or more elements such as bismuth, gold, gadolinium, and/or other elements with K-edge values within the diagnostic x-ray energy band. An example contrast material that targets macrophages is discussed in "Atherosclerotic Plaque Composition: Analysis with Multicolor CT and Targeted Gold Nanoparticles," Cormode, et al., 2010 Radiology: Volume 256: Number 3. Other contrast materials are also contemplated herein.

A radiation source 112, such as an x-ray tube, is supported by and rotates with the rotating gantry 104 and is configured to emit poly-energetic radiation. A detector array 116 includes one or more rows of detector pixels that detect radiation that traverses the examination region 106. The illustrated detector array 116 includes one or more energy-resolving detectors such as direct conversion detectors (e.g., CdTe, CdZnTe, etc.) or a scintillator-based multi-spectral detector with at least two scintillators having different x-ray energy sensitivities and at least two corresponding photosensors having corresponding optical sensitivities. The detector array 116 generates an electrical signal indicative of the detected radiation.

A signal decomposer 118 decomposes the energy-resolved signals into various energy dependent components. For example, in one instance a detected energy-resolved signal is decomposed into a Compton component, a photoelectric component, and/or one or more K-edge components representative of one or more K-edge materials, for example, in a contrast material. An example decomposition approach is described in application serial number PCT/IB2007/055105, filed on Dec. 14, 2007, which claims the benefit of provisional application Ser. No. EP 06126653.2, filed on Dec. 20, 2006, both of which are incorporated in their entirety herein by reference.

A reconstructor 120 reconstructs signals generated by the detector array 116, generating volumetric image data. In one instance, this includes reconstructing the Compton, photoelectric, and/or K-edge components, individually or in combination. With embodiments in which the contrast agent includes a K-edge material, the K-edge component can be reconstructed to generate a contrast material image representative of the tissue of interest. One or more anatomical structural images of the tissue of interest may also be reconstructed based on one or more of the decomposed components. Furthermore, a contrast material image and a structural image may be combined in a single image and/or displayed next to each other.

A general purpose computer serves as an operator console 122. The console 122 includes a human readable output device such as a monitor or display and an input device such as a keyboard, mouse, etc. Software resident on the console 122 allows the operator to interact with the imaging system 100 via a graphical user interface (GUI) or otherwise. This interaction may include selecting an imaging protocol such as a contrast enhanced imaging protocol, initiating scanning, etc.

An analyzer 124 analyzes volumetric image data. As described in greater detail below, in one non-limiting instance the analysis includes analyzing one or more contrast enhanced images corresponding to a contrast material that targets scar tissue created during and/or after ablation of tissue of interest and generating a signal indicative whether the ablation of the tissue of interest is complete based on the one or more images. The signal can be used to determine whether further ablation should be performed, for example, where the cardiac catheter ablation of the tissue of interest is not suitable. The signal can be presented via a display 126 or the like through quantified indicia (e.g., a numerical value, a color, etc.), in an image (e.g., a K-edge image, a K-edge image superimposed over a structural image, etc.), in a plot/graph, etc.

A data repository 128 can be used to store the image data generated by the system 100, the signal generated by the analyzer 124 and/or other information from another device. The data repository 128 may include one or more of a picture archiving and communication system (PACS), a radiology information system (RIS), a hospital information system (HIS), an electronic medical record (EMR) database, a sever, a computer, and/or other data repository. The data repository 128 can be local to the system 100 or remote from the system 100.

It is to be appreciated that the analyzer 124 can be implemented via a processor executing one or more computer readable instructions encoded or embedded on computer readable storage medium such as physical memory. Such a processor can be part of the console 122 and/or other computing device such as a dedicated visualization computer, and/or other computing device. The processor can also execute at least one computer readable instructions carried by a carrier wave, a signal, or other non-computer readable storage medium such as a transitory medium.

FIG. 2 illustrates an example of the analyzer 124.

In this example, the analyzer 124 is described in connection with contrast enhanced image data indicative of a contrast material targeted to scar tissue created during and/or after ablation such as cardiac catheter ablation of tissue of interest, tumor ablation and/or other ablation.

An image combiner 202 combines (e.g., superimposes, overlay, etc.), in one non-limiting instance, the contrast enhanced image representative of the scar tissue and a structural image of the same anatomy into a signal image. The analyzer 124 can output the contrast enhanced image, the structural image and/or the single image.

Optionally, a quantifier 204 quantifies an amount of contrast material in the contrast enhanced image, for example, the amount along the tissue of interest. The analyzer 124 can combine the quantified amount and the contrast enhanced image and/or the single image, and/or output the quantified amount and/or combined data.

Optionally, a comparator 206 compares the quantified amount of contrast material along the tissue of interest with one or more predetermined thresholds 208. A recommender 210 generates a signal indicative of a recommendation based at least on a result of the comparison and one or more rules 212. In the illustrated embodiment, the recommender 210 generates the recommendation based on one or more rules 212.

By way of example, a rule may indicate that if the amount or level of contrast agent is less than a threshold value, then the recommender 210 will generate a signal indicating that the further ablation should be performed. The rule and/or another rule may indicate that if the amount or level of contrast agent is greater than the threshold value, then the recommender 210 will generate a signal indicating that the ablation is complete.

A suitable recommendation may also be no recommendation or absence of a recommendation. In this case, the signal may not even be generated. In some embodiments, the recommender 210 is omitted.

In FIG. 1, the analyzer 124 analyzes contrast enhanced CT data. In a variation, the analyzer 124 can analyze contrast enhanced x-ray data to evaluate a result of a cardiac catheter ablation.

FIG. 3 illustrates an example method for evaluating a result of ablation of tissue of interest.

It is to be appreciated that the ordering of the acts in the methods described herein is not limiting. As such, other orderings are contemplated herein. In addition, one or more acts may be omitted and/or one or more additional acts may be included.

At 302, ablation is performed for tissue of interest in a first examination room. The ablation can be radio frequency or cryogenic ablation. The tissue of interest can be, for example, cardiac catheter ablation or ablation of a tumor.

At 304, a contrast enhanced CT or x-ray scan of the tissue of interest is performed to image contrast material targeted to scar tissue created by the ablation in the tissue of interest. The contrast enhanced scan can be performed in the same or a different examination room.

At 306, an amount of the contrast material is quantified for the scar tissue of the tissue of interest based on a contrast enhanced image from the scan.

At 308, the quantified amount of contrast material is compared against one or more pre-determined thresholds.

At 310, a recommendation, which indicates whether further ablation is recommended, is generated based on a result of the comparison and one or more rules.

At 312, optionally, at least one of the recommendation, the quantified amount of contrast material, the contrast enhanced image, or a combination of the contrast enhanced image and a structural image of the tissue of interest from the scan is visually presented.

As discussed herein, the information presented herein can be used to facilitate determining whether or not further cardiac catheter, tumor, etc. ablation should be performed.

The methods described herein may be implemented via one or more processors executing one or more computer readable instructions encoded or embodied on computer readable storage medium such as physical memory which causes the one or more processors to carry out the various acts and/or other functions and/or acts. The one or more processors can also execute instructions carried by transitory medium such as a signal or carrier wave.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An analyzer, comprising:
a quantifier, comprising processor circuitry, configured to quantify an amount of contrast material in contrast enhanced imaging data generated by a computed tomography imaging scanner emitting poly-energetic x-ray radiation;
a comparator, comprising the processor circuitry, configured to compare a quantified amount with a pre-determined threshold; and
a recommender, comprising the processor circuitry, configured to generate a signal indicative of a recommendation to further ablate the tissue of interest in response to the quantified amount of the contrast material not satisfying a pre-determined threshold, wherein the recommender is configured to generate the signal based on a result of a comparison and one or more rules.

2. The analyzer of claim 1, wherein the contrast enhanced imaging data include computed tomography contrast enhanced imaging data.

3. The analyzer of claim 1, wherein the contrast enhanced imaging data include x-ray contrast enhanced imaging data.

4. The analyzer of claim 1, wherein the ablation is one or more of radio frequency or cryogenic ablation.

5. The analyzer of claim 1, wherein the tissue of interest is cardiac tissue.

6. The analyzer of claim 1, wherein the tissue of interest is a tumor.

7. The analyzer of claim 1, wherein the recommender is configured to generate a signal indicative of a recommendation when there is the recommendation, and the recommender is configured not to generate a signal indicative of a recommendation when there is no recommendation.

8. The analyzer of claim 1, further comprising:
a combiner, comprising the processor circuitry, configured to combine a contrast image representing the contrast material of the tissue of interest and a structural image of the tissue of interest, wherein a combination of the images is visually presented.

9. The analyzer of claim 8, wherein the contrast image represents a nano-particle contrast material targeted to at least one of the scar tissue.

10. The analyzer of claim 9, wherein the nano-particle contrast material includes one or more of bismuth, gold, or gadolinium nano-particles.

11. The analyzer of claim 8, wherein the quantified amount is presented along with the contrast enhanced image.

12. The analyzer of claim 8, wherein the quantified amount is visually represented in a graph.

13. The analyzer of claim 8, wherein the signal indicative of the recommendation is presented along with the contrast enhanced image.

14. The analyzer of claim 8, wherein the combiner is configured to generate a single imaging data by combining the contrast image representing the contrast material of the tissue of interest and the structural image of the tissue of interest.

15. A method, comprising:
obtaining, by processor circuitry, contrast enhanced image data indicative of scar tissue created by ablation of tissue of interest, wherein the contrast enhanced image data is generated by a computed tomography imaging scanner emitting poly-energetic x-ray radiation;
quantifying, by the processor circuitry, an amount of contrast material for the scar tissue in the tissue of interest;
generating, by the processor circuitry, a signal indicative of a recommendation to further ablate the tissue of interest in response to a quantified amount of the contrast material not satisfying a pre-determined threshold, by comparing the quantified amount with the pre-determined threshold using one or more rules;
combining, by the processor circuitry, a contrast image representing the contrast material of the tissue of interest and a structural image of the tissue of interest; and
visually presenting, by the processor circuitry, at least a combination of the images.

16. The method of claim 15, wherein the contrast enhanced imaging data includes at least one of computed tomography contrast enhanced imaging data or x-ray contrast enhanced imaging data.

17. The method of claim 15, wherein the contrast material includes a nano-particle contrast material targeted to at least one of the scar tissue.

18. The method of claim 17, wherein nano-particles include one or more of bismuth, gold, or gadolinium nano-particles.

\* \* \* \* \*